United States Patent [19]

Takeichi et al.

[11] Patent Number: 5,068,187
[45] Date of Patent: Nov. 26, 1991

[54] PROCESS FOR PRODUCING D-α-AMINO ACIDS

[75] Inventors: Mamoru Takeichi; Naoshi Hagihara; Hitoshi Tarukawa; Shinichirou Tawaki, all of Chiba; Nobuyoshi Makiguchi, Kanagawa, all of Japan

[73] Assignee: Mitsui Toatsu Chemicals, Inc., Tokyo, Japan

[21] Appl. No.: 332,426

[22] Filed: Mar. 28, 1989

Related U.S. Application Data

[63] Continuation of Ser. No. 840,133, Mar. 17, 1986, abandoned.

[30] Foreign Application Priority Data

Mar. 19, 1985 [JP] Japan .................. 60-053396

[51] Int. Cl.$^5$ .................. C12P 13/04; C12P 13/12; C12P 13/06; C12N 13/16
[52] U.S. Cl. .................. 435/106; 435/113; 435/116; 435/115; 435/108; 435/280; 435/255
[58] Field of Search .................. 435/106, 280, 255, 116, 435/107, 108, 171, 115, 911, 930

[56] References Cited

U.S. PATENT DOCUMENTS 4,237,227 12/1980 Yamada et al. .................. 435/106 X

FOREIGN PATENT DOCUMENTS 204253 9/1980 United Kingdom .

OTHER PUBLICATIONS

Lodder "The Yeasts", 1970, N. Holland Publ. Co. pp. 894-898, pp. 26-31 and 17.
Chemical Abstracts, vol. 106, Abstract no. 17043w, Jan. 1987, p. 478.

*Primary Examiner*—Douglas W. Robinson
*Assistant Examiner*—Irene Marx
*Attorney, Agent, or Firm*—Browdy and Neimark

[57] ABSTRACT

The 5-substituted hydantoins represented below can be transformed into D-α-amino acids by the use of the cultured broth, cells or treated cells of the genus Hansenula:

5-substituted hydantoins:

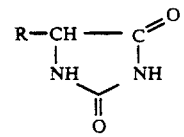

wherein R represents an alkyl, substituted alkyl, phenyl or substituted phenyl group.

D-α-amino acids:

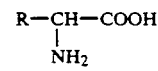

wherein R represents the same meanings as above.

4 Claims, No Drawings

PROCESS FOR PRODUCING D-α-AMINO ACIDS

This application is a continuation of application Ser. No. 06/840,133, filed Mar. 17, 1986, now abandoned.

FIELD OF THE INVENTION

This invention concerns a process for producing D-α-amino acids with an extreme advantage by using the genus Hansenula having a capability of transforming 5-substituted hydantoins into D-α-amino acids.

PRIOR ART AND THE PROBLEMS THEREIN

As one of the methods for producing D-α-amino acids, there has been known a process of chemically hydrolyzing a corresponding 5-substituted hydantoin into DL-α-amino acids and then optically resolving the mixture into a D-α-amino acid. However, the step for the optical resolution is particularly troublesome and the yield is not so high in this process. Further, there has been known a process for producing a D-α-amino acid by subjecting a 5-substituted hydantoin to the action of a cultured broth, cells, treated cells or enzyme of microorganisms to prepare an optically active N-carbamoyl-D-α-amino acid, which is then converted into D-α-amino acid by the treatment with a solution of sodium nitrite.

However, the reaction step and the purification step are troublesome also in this process.

Furthermore, a process is also known for directly obtaining a D-α-amino acid by subjecting a 5-substituted hydantoin to the action of a cultured broth, cells or treated cells of microorganisms, for example, the genera Pseudomonas, Moraxella, Paracoccus, Arthrobacter, Alcaligenes, Flavobacterium. However, the yield is low also in this process.

MEANS FOR THE RESOLUTION OF THE PROBLEMS

The present inventors have made a study in order to find a process with a better efficiency than that of the conventional production process and, as a result, have found that the genus Hansenula has a capability of transforming 5-substituted hydantoins into D-α-amino acids. It has not been hitherto known that the genus Hansenula has a capability of transforming 5-substituted hydantoins into D-α-amino acids. This invention has been accomplished as a result of our study further made on the foregoing finding.

That is, this invention concerns a process for producing D-α-amino acids represented by the general formula:

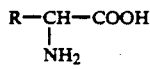
 (I)

(where R represents an alkyl group, substituted alkyl group, phenyl group or substituted phenyl group) by subjecting 5-substituted hydantoins represented by the general formula:

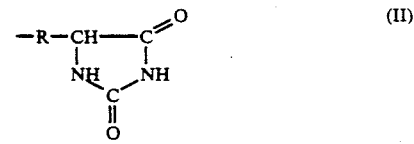
 (II)

(where R represents the same meanings as in the formula (1)).

Microorganisms employed in the present invention are, for example, *Hansenula ciferrii, Hansenula henricii, Hansenula nonfermentaus, Hansenula polymorpha*, which may be microorganisms of wild strains present in the nature or those preserved in public microorganism preservation organizations so long as they are used for the purpose of this invention. As a method of testing microorganisms having a capability of transforming 5-substituted hydantoins into D-α-amino acids, the following method can be employed for instance. After collecting 5 ml of a cultured broth of microorganisms to be tested and collecting the cells by centrifugation, the collected cells are washed with an equivalent volume of sterilized saline, dispersed into 2 ml of a substrate solution of D-isopropyl hydantoin at 0.5% by weight of concentration in a potassium phosphate buffer (0.1M concentration, pH=7.5) and then reacted for 24 hours. Then, the reaction solution was centrifugated at 10,000 rpm for 10 minutes to obtain a supernatant liquid, which is then separated on paper chromatography (developing solution:Bu-OH:acetic acid:water:=4:1:1). Then, ninhydrin chromophoric reaction is carried out and the color-developed portion is cut out and extracted with a 5 ml of 75% ethanol solution, followed by colorimetry at a wavelength of 570 nm.

The strains recognized as capable of transforming the hydantoin into the amino acid as described above were tested by further isolating and purifying the thus formed amino acid and measuring the optical rotation. The genus Hansenula usable in this invention are those passing the aforementioned test.

The 5-substituted hydantoins usable in this invention are those in which the hydrogen atom at 5-position on the hydantoin is substituted with an alkyl group, phenyl group or substituted derivative thereof. The substituent groups attached to the alkyl or phenyl group can include, for example, halogen atom, alkylmercapto group, hydroxy group, alkoxy group, amino group, indolyl group and alkoxycarbonyl group. 5-substituted hydantoins usable in this invention and D-amino acids corresponding to the respective hydantoins can be represented specifically as shown in Table 1.

TABLE 1

| 5-substituted hydantoin | Substituents R for hydantoin | Corresponding α-amino acid |
|---|---|---|
| 5-methylhydantoin | $CH_3-$ | alanine |
| 5-chloromethylhydantoin | $ClCH_2-$ | β-chloroalanine |
| 5-n-propylhydantoin | $CH_3CH_2CH_2-$ | norvaline |

TABLE 1-continued

| 5-substituted hydantoin | Substituents R for hydantoin | Corresponding α-amino acid |
|---|---|---|
| 5-iso-propylhydantoin | 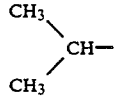 | valine |
| 5-n-butylhydantoin | $CH_3CH_2CH_2CH_2-$ | norleucine |
| 5-iso-butylhydantoin | 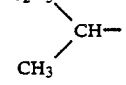 | isoleucine |
| 5-sec-butylhydantoin | 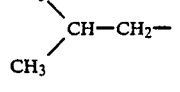 | leucine |
| 5-methylthioethyl-hydantoin | $CH_3S-CH_2CH_2-$ | methionine |
| 5-hydroxymethyl-hydantoin | $OHCH_2-$ | serine |
| 5-1-hydroxyethyl-hydantoin | 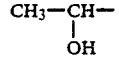 | threonine |
| 5-phenyl-hydantoin |  | phenylglycine |
| 5-p-hydroxyphenyl-hydantoin | 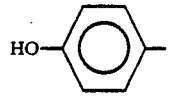 | p-hydroxyphenylglycine |
| 5-benzyl-hydantoin | 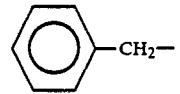 | phenylalanine |
| 5-3-aminopropyl-hydantoin | $NH_2CH_2CH_2-$ | methionine |
| 5-indolylmethyl-hydantoin | 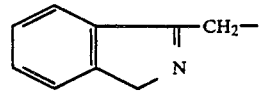 | tryptophan |
| 5-2-carboxyethyl-hydantoin | $HOOC-CH_2CH_2-$ | glutamic acid |

The genus Hansenula acts on 5-substituted hydantoins in this invention by bringing the cells or treated cells into contact with hydantoins in an aqueous solution.

The culture mediums usable for the cultivation of the microorganisms include those ordinary culture mediums usually containing a digestable carbon source and nitrogen source, as well as nutrients of inorganic salts required for the growth of the microorganisms. The cultivation may be carried out under aerobic conditions while appropriately controlling the pH from 4 to 9 and temperature from 25° to 45° C.

In the enzymatic reaction, the usable concentration of substrate ranges from 0.1 to 10% by weight. The temperature optimum to the enzyme in the microorganisms employed having a capability of converting into D-α-amino acids is used as the reaction temperature and it usually ranges from 25° to 60° C. A pH value optimum to the enzyme in the microorganisms having the capability of transforming into D-α-amino acids is used as the pH during reaction and it usually within a range of pH=5-9. Particularly preferably, the temperature is from 20° to 50° C. and pH=6-8.5. D-α-amino acids prepared by asymmetrically transforming 5-substituted hydantoins as described above can be separated and converted into aimed D-α-amino acids by utilizing known methods such as concentration, neutralization and ion exchange.

FUNCTION AND EFFECT OF THE INVENTION

Since D-α-amino acids can easily be prepared from 5-substituted hydantoins by using the genus Hansenula in this invention, it is an extremely advantageous process for producing D-α-amino acids.

EXAMPLE

This invention will now be described more specifically referring to the following examples, but the invention is no way limited only to these examples.

EXAMPLE 1

A culture medium of a composition shown in Table 2 was filled by an amount of 20 ml into a 250 ml of an Erlenmyer flask, sterilized at 120° C. for 15 minutes and mixed with DL-5-isopropyl hydantoin separately sterilized. Then, *Hansenula polymorpha* (NRRL Y-2423) cultured in a yeast YM culture medium at 28° C. for 40 hours was inoculated by a spoonful of platinum spatula at 28° C. for 24 hours. The culture solution was centrifugated to collect cells and washed once with sterilized saline water in an amount equivalent to the culture liquid to collect the cells. The cells were added to 0.1M sodium phosphate buffer (pH=7.5) containing 5 g/liter of one of 5-substituted hydantoins shown in Table-3 up to the amount of 30 g/liter, 5 ml of which were reacted at 36° C. for 20 hours. As the result of measuring the thus formed various kinds of amino acids by the foregoing method and further separating and purifying the amino acids to measure the optical rotation, it was confirmed that the resulted amino acids were D-body in all of the cases. The results are shown in Table 3.

TABLE 2

| Name of substance | Concentration (g/l) |
| --- | --- |
| Glucose | 20 |
| DL-isopropylhydantoin | 5 |
| Malt extract | 1 |
| Yeast extract | 3 |
| KH$_2$PO$_4$ | 1.5 |
| MgSO$_4$.7H$_2$O | 0.5 |
| CaCl$_2$.2H$_2$O | 0.33 |
| pH = 6 | |

TABLE 3

| Reaction substrate | Product | Production amount (mg/ml) |
| --- | --- | --- |
| 5-methylhydantoin | D-alanine | 0.3 |
| 5-isopropylhydantoin | D-valine | 0.5 |
| 5-isobutylhydantoin | D-leucine | 0.7 |
| 5-sec butylhydantoin | D-isoleucine | 0.4 |
| 5-methylthioethyl hydantoin | D-methionine | 0.4 |
| 5-hydroxymethyl hydantoin | D-serine | 0.2 |
| 5-phenylhydantoin | D-phenylglycine | 1.0 |
| 5-p-hydroxyphenyl hydantoin | D-p-hydroxyphenyl glycine | 0.8 |
| 5-benzylhydantoin | D-phenylalanine | 0.8 |
| 5-indolylmethyl hydantoin | D-tryptophan | 0.1 |

EXAMPLE 2

A culture medium of a composition shown in Table-2 was filled by an amount of 20 ml into a 250 ml of Erlenmyer flask, sterilized at 120° C. for 15 minutes and mixed with DL-5-isopropyl hydantoin separately sterilized. Then, microorganisms shown in Table 4, which had been cultured in a yeast YM culture medium at 28° C. for 40 hours, were inoculated by a spoonful of platinum spatula at 28° C. for 24 hours. The cells were centrifugated from the culture liquid and applied with the same procedures as in Example 1 to collect the cells. The cells were added to a 0.1M potassium phosphate buffer (pH=7.5) containing 5 g/liter of 5-phenylhydantoin, 30 g/liter, 5 ml of which were reacted at 36° C. for 20 hours. After the reaction, the separation and purification were made in the same manner as in Example 1 and the results of the analysis are shown in Table 4.

TABLE 4

| Strains used | | Production amount of D-phenylglycine (mg/ml) |
| --- | --- | --- |
| *Hansenula polymorpha* | NRRL Y-2423 | 1.0 |
| *Hansenula polymorpha* | CBS-7031 | 0.8 |
| *Hansenula ciferrii* | ATCC-14091 | 0.3 |
| *Hansenula henricii* | ATCC-18939 | 0.5 |
| *Hansenula henricii* | CBS-5765 | 0.4 |
| *Hansenula nonfermentans* | ATCC-18937 | 0.2 |

What is claimed is:

1. A process for producing D-alpha-amino acid represented by formula (I):

where R represents a phenyl group; a hydroxyphenyl group; an unsubstituted C$_1$-C$_4$ alkyl group or a substituted C$_1$-C$_2$ alkyl group wherein the substituent is methylthio, hydroxy, phenyl or indolyl; comprising the steps of:

subjecting a 5-substituted hydantoin represented by formula (II):

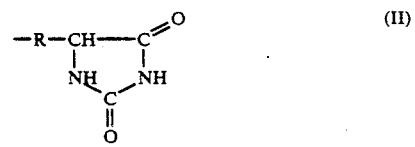

where R represents the same meaning as in the formula (I), to the action of a cultured broth or cells of a microorganism having the ability to microbially transform said hydantoin of formula (II) into a D-α-amino acid of formula (I), said microorganism being selected from the group consisting of *Hansenula ciferrii*, *Hansenula henricii*, *Hansenula nonfermentans* and *Hansenula polymorpha*; and purifying the thus obtained D-α-amino acid.

2. The process of claim 1, wherein the D-α-amino acid represented by formula (I) is phenylglycine.

3. The method of claim 1 wherein said microorganism is *Hansenula polymorpha*.

4. The method of claim 1 wherein said microorganism is cultured at about 28° C.

* * * * *